United States Patent [19]

Rosenberg et al.

[11] 4,177,263

[45] Dec. 4, 1979

[54] ANTI-ANIMAL TUMOR METHOD

[75] Inventors: Barnett Rosenberg, Holt; Loretta VanCamp, East Lansing; Thomas Krigas, Okemos, all of Mich.

[73] Assignee: Research Corporation, New York, N.Y.

[21] Appl. No.: 754,512

[22] Filed: Dec. 27, 1976

Related U.S. Application Data

[63] Continuation of Ser. No. 405,184, Oct. 10, 1973, abandoned, which is a continuation of Ser. No. 230,533, Feb. 28, 1972, abandoned, which is a continuation of Ser. No. 30,239, Apr. 20, 1976, abandoned.

[51] Int. Cl.$^2$ .................... A61K 33/24; A61K 31/28

[52] U.S. Cl. ...................................... 424/131; 424/287

[58] Field of Search .............................. 424/287, 131

[56] References Cited

PUBLICATIONS

Rossof et al., Cancer Treatment Reports, vol. 60, No. 11, Nov. 1976, pp. 1679–1680.

*Primary Examiner*—Jerome D. Goldberg
*Attorney, Agent, or Firm*—Dennis P. Clarke

[57] ABSTRACT

Malignant tumors in animals are treated by parenterally administering to an affected animal a solution containing a complex compound of platinum in an amount effective to cause regression of the tumor.

4 Claims, No Drawings

ANTI-ANIMAL TUMOR METHOD

This is a continuation, of application Ser. No. 405,184, filed Oct. 10, 1973 now abandoned, which is a Continuation of application Ser. No. 230,533 filed Feb. 28, 1972, now abandoned, which is a continuation of application Ser. No. 30,239 filed Apr. 20, 1976 now abandoned.

This invention relates to a method for treating tumors in animals.

We have discovered that complex compounds of platinum cause regression of malignant tumors in animals. More specifically, the present invention is a method for treating malignant tumors in animals which comprises parenterally administering to an animal affected with a malignant tumor a solution containing a complex compound of platinum in an amount sufficient to cause regression of the tumor.

The complex compounds of platinum useful in practicing the method of the present invention may be organic, inorganic or mixed. Organic complexes are most conveniently prepared by the reaction of a platinum salt with polyfunctional organic compounds such as beta-diketones, alpha-aminoacids, alpha-hydroxyacids and others usually designated as chelating agents. Platinum ion is incorporated into the chelating agents to form neutral coordination compounds or chelates. Suitable organic coordination compounds of platinum and methods for their preparation are described by Martell and Calvin, Chemistry of Metal Chelate Compounds, Prentice-Hall, Inc., Englewood Cliffs, N.J. (1952), by Bailar, The Chemistry of Coordination Compounds, Reinhold Publishing Co., New York (1956), and by Dwyer and Mellar, Chelating Agents and Metal Chelates, Academic Press, Inc., New York (1964).

Inorganic complex compounds of platinum useful in practicing the method of the present invention may be neutral or positively or negatively charged. Platinum (II) forms $dsp^2$ complexes which are generally planar; platinum (IV) forms $d^2sp^3$ complexes which are octahedral. Depending on the number of substituents present and their location, these complexes can exist as cis and trans isomers. Suitable inorganic coordination compounds of platinum and methods for their preparation are described by Kauffman, Inorganic Synthesis, 7, McGraw-Hill Book Co., Inc., New York (1963), Chemical Abstracts, 44, 5257 g (1950) and in the references cited above.

Coordination compounds of platinum wherein the donor groups or ligands are Cl, Br, CN, $NO_3$, $NH_3$, en, pn, pyr, $H_2O$, OH, OR, OS and the like are preferred; bidentate ligands, such as ethylene diamine (en) and propylene diamine (pn), form two coordinate covalent bonds with the central platinum ion. Coordination compounds wherein the ligands are ammonia and chloro, preferably wherein two chloros are cis to each other, are particularly preferred for use in practicing the method of the present invention. A list of suitable chloroplatinumammines would include.

| Complex | Charge |
|---|---|
| trichloroamineplatinate(II) | − |
| cis- and trans-dichlorodiamineplatinum(II) | |
| chlorotriamineplatinum(II) | + |
| tetraamineplatinum(II) | ++ |
| pentachloroamineplatinate(IV) | − |
| cis- and trans-tetrachloroamineplatinum(IV) | |
| trichlorotriamineplatinum(IV) | + |
| dichlorotetraamineplatinum(IV) | ++ |
| ammonium tetrachloroplatinate | |

It is understood that complexes bearing a charge exist in the solid state as salts in conjunction with appropriate oppositely charged ions, e.g., negatively charged complexes are generally prepared as ammonium or alkali metal salts and positively charged complexes are generally prepared as halides.

The platinum complexes were obtained commercially or prepared, and purified by crystallization and stored in the dark until required for testing. Test solutions were freshly prepared just prior to use by dissolving the text complex in physiological saline or in the buffered "C" medium of Roberts et al, Carnegie Inst. Wash. Publ., 607, 5, (1955); it has been found that the presence of salt in such solutions tends to stabilize the complex. The complex-containing solutions were tested for anti-tumor activity in animals in accordance with the Cancer Chemotherapy National Service Center (CCNSC) Protocols for screening of chemical agents and natural products against animal tumors and other biological systems, Cancer Therapy Reports, 25, (1962) and Venditti et al, Lloydia, 30, 332 (1967), against representative malignant tumors Sarcoma 180 and mouse leukemia L1210. Our method is further illustrated but not limited to those chloroplatinumammines exhibiting superior anti-tumor activity.

Following CCNSC Protocols, cis-Pt(II)(NH$_3$)$_2$Cl$_2$ and cis-Pt(IV)(NH$_3$)$_2$Cl$_4$ were tested against mouse leukemia L1210. Two successive tests were run, the first on 19-24 gram male hybrid mice BDF$_1$[(C57Bl/6×DBA/2)F$_1$], and the second with 17-20 gram females of the same strain, using ten animals per dose level and 40 untreated controls. The mice were injected intraperitoneally with a saline suspension from DBA/2 stock tumor mice with 10$^5$ cells of L1210 ascites per mouse on day 0 and with 0.5 ml. test solution beginning on day 1. The mice were observed through day 30; therapeutic efficacy was measured by the increase in mean survival time of treated mice over the 9.5 days mean survival time of the untreated controls. The surviving mice were found tumor-free on gross examination. The results of these tests are summarized below.

| Test Compound | Daily Dose | Mean Weight Change (days 1–5)g | % Increase In Mean Survival Time |
|---|---|---|---|
| cis-Pt(IV)(NH$_3$)$_2$Cl$_4$ | 2.5 mg/kg in buffer given days 1–9 | −3.3 | 38 |
| | 2.5 mg/kg in saline given days 1–9 | −2.2 | 49 |
| cis-Pt(II)(NH$_3$)$_2$Cl$_2$ | 1.25 mg/kg in buffer given days 1–9 | −2.7 | 87 |
| | 1.25 mg/kg in saline given days 1–9 | −2.7 | 44 |
| | 5 mg/kg in saline given day 1 | −1.4 | 59 |
| | 10 mg/kg in saline given | | |

| Test Compound | Daily Dose | Mean Weight Change (days 1–5)g | % Increase In Mean Survival Time |
|---|---|---|---|
| | day 1 | −3.6 | 83 |

Following CCNSC Protocols, cis- and trans-Pt(IV)(NH$_2$)$_2$Cl$_4$, [Pt(IV)(NH$_3$)$_3$Cl$_3$]Cl and (NH$_4$)$_2$Pt(IV)Cl$_6$ were tested against Sarcoma 180. Each compound was tested at four dose levels tolerated by the mice over the period of testing. The Sarcoma 180 tumor bearing mice were provided by the Henry Ford Hospital, Detroit, Mich.; the tumors were transferred serially to form a stock tumor supply in random bred 18–22 gram female Swiss white mice. Six mice in each dose level were inoculated with the tumor transplants on day 0. Treatment with the test compounds began day 1 and extended in most tests to day 10. The test compounds were dissolved in saline or buffer as indicated and administered intraperitoneally to give the dose indicated. The controls were not inoculated and no positive controls were utilized. The mice were observed and weighed daily. On day 10 most of the animals were sacrificed, the tumors excised, debrided, weighed and averaged. Some animals were kept alive at the termination of the test and appeared grossly tumor-free for two months. Palpitation indicated that the initial tumor transplant had disappeared; and mice exhibited normal weight gain and appeared healthy. The results of these tests are summarized below:

| Test Compound | Daily Injection Dose mg/kg | Mean Weight Change g | T/C × 100 |
|---|---|---|---|
| cis-Pt(IV)(NH$_3$)$_2$Cl$_4$ | 0.59 | +2.1 | 113.8 |
| | 1.18 | −0.3 | 27.0 |
| in saline | 2.37 | −1.7 | 26.2 |
| | 4.75 | −5.7 | 4.5 |
| | (days 1–10) | | |
| cis-Pt(IV)(NH$_3$)$_2$Cl$_4$ | 0.59 | +1.9 | 58.4 |
| | 1.18 | +0.6 | 46.9 |
| in buffer | 2.37 | −3.7 | 30.9 |
| | 4.75 | −5.3 | 8.3 |
| | (days 1–10) | | |
| Control | | +4.2 | [309mg]* |
| [Pt(IV)(NH$_3$)$_3$Cl$_3$]Cl | 1.01 | +4.6 | 107.7 |
| | 2.03 | +3.3 | 71.5 |
| in buffer | 4.06 | +2.6 | 61.6 |
| | 8.12 | +2.4 | 49.9 |
| | (days 1–10) | | |
| Control | | +5.0 | [212mg]* |
| (NH$_4$)$_2$Pt(IV)Cl$_6$ | 11.4 | +1.0 | 33.5 |
| in buffer | 17.0 | +0.4 | 16.0 |
| | 22.8 | 0 | 12.1 |
| | (days 1–10) | | |
| Control | | +4.4 | [369 mg]* |
| cis-Pt(IV)(NH$_3$)$_2$Cl$_4$ | 4.76 | +1.4 | 7.7 |
| in buffer | (days 1 and 2 only) | | |
| Control | | +6.8 | [435mg]* |
| Trans-Pt(IV)(NH$_3$)$_2$Cl$_4$ | 2.38 | +4.8 | 43.8 |
| in buffer | 4.76 | +5.6 | 43.0 |
| | 9.51 | +4.4 | 37.1 |
| | (days 1 and 2 only) | | |
| Control | | +4.4 | [369mg]* |

*Mean control tumor weight.

In another series of experiments following CCNSC Protocols, cis-Pt(IV)(NH$_3$)$_2$Cl$_4$, Cis-Pt(II)(NH$_3$)$_2$Cl$_2$, Pt(II)(NH$_2$CH$_2$CH$_2$NH$_2$)Cl$_2$, and Pt(IV)(NH$_2$CH$_2$CH$_2$NH$_2$)Cl$_4$ were screened against Sarcoma 180 using ICR mice and a tumor line provided by the National Institutes of Health. The indicated doses of these test compounds were injected intraperitoneally into mice as a 0.5 ml. solution in physiological saline or buffer. Therapeutic efficacy was measured by the ratio $$\frac{\text{Treated tumor mass}}{\text{Control tumor mass}} \times 100 \ (T/C \times 100).$$

Inanition, based on the recorded weight losses, could cause at most a T/C×100 value of 50. Several of the surviving mice were retained for 6 months and appeared healthy and tumor-free; palpitation indicated that the initial tumor transplant had disappeared. The results of these experiments are summarized below:

| Test Compound | Dose mg/kg | Weight Loss | T/C × 100 |
|---|---|---|---|
| Cis-Pt(IV)(NH$_3$)$_2$Cl$_4$ | 2.5 | −4.3 | 83 |
| | 5.0 | −1.6 | 63 |
| | 10.0 | −1.8 | 29 |
| | Control | −2.2 | (825 mg)* |
| Cis-Pt(II)(NH$_3$)$_2$Cl$_2$ | 0.5 | +0.3 | 75 |
| | 1.0 | −4.3 | 44 |
| | 2.0 | −5.6 | 1.8 |
| | Control | +1.1 | (524 mg)* |
| Pt(II)(en)Cl$_2$ | 1.25 | −2.3 | 17 |
| | 2.5 | −3.6 | 13 |
| | 5.0 | 5.4 | 3.6 |
| | Control | +1.1 | (524 mg)* |
| Pt(IV)(en)Cl$_4$ | 0.62 | −1.1 | 54 |
| | 1.25 | −3.8 | 32 |
| | 2.5 | −5.2 | 23 |
| | 5.0 | −5.4 | 20 |
| | Control | +1.1 | (524 mg)* |

*Mean control tumor weight.

In another series of experiments following CCNSC Protocols, random bred germ-free Swiss white mice obtained from Spartan Research Laboratories, Williamston, Mich., were implanted with a Sarcoma 180 tumor originally obtained from the National Institute of Health. The tumor line was passed through 18 transplantations in ICR mice and then through six further transplantations in random bred, germ-free, Swiss white mice. Preliminary tests with these compounds on large solid Sarcoma tumors indicated approximately a 60% regression rate based on average cage weights for both male and female ICR and Swiss white mice having an individual weight of 17–22 grams at the start of the test. Improved results were obtained by using a smaller gauge needle (#26) to minimize the forcing out of injected fluid by muscular contraction, particularly in the case of single injections. In addition, the animals were weighed individually just prior to injection and the doses were administered on an individual animal weight basis.

The experiment included 36 control animals. Of these 12 were sacrificed on day 8 (the day of first treatment tumor implant was on day 0) and the tumors were excised and weighed to determine the average control tumor size of the animals in the experiment. Twelve mice with the smallest tumors were removed from the group thereby biasing the experiment in favor of larger initial tumors (no tumor weighed less than 0.5 g. and the average tumor weight was about 0.96 g.). The remaining 72 mice were divided randomly into cages of 6 each for the various dose schedules indicated. The animals were observed and weighed daily. The results obtained in the series of experiments are summarized below:

| Compound | Dose Schedule | Deaths | Regressions |
|---|---|---|---|
| Cis-Pt(II)(NH$_3$)$_2$Cl$_2$ | 2.0 mg/kg daily | 6 | 0 |
| " | 4.0 mg/kg day 8 | 5 | 1 |
| " | 4.0 mg/kg days 8 & 17 | 1 | 5 |
| " | 6.0 mg/kg day 8 | 2 | 4 |
| " | 6.0 mg/kg days 8 & 16 | 3 | 3 |
| " | 8.0 mg/kg day 8 | 0 | 6 |
| Cis-Pt(IV)(NH$_3$)$_2$Cl$_4$ | 4.0 mg/kg daily | 5 | 1 |
| " | 6.0 mg/kg day 8 | 5 | 1 |
| " | 6.0 mg/kg days 8 & 15 | 3 | 3 |
| " | 8.0 mg/kg day 8 | 3 | 3 |
| " | 8.0 mg/kg days 8, 16 & 23 | 1 | 5 |
| " | 10.0 mg/kg day 8 | 5 | 1 |
| Controls (regression spontaneous) | | 20 | 4 |

The controls exhibited 4 spontaneous regressions of the tumor out of 24 animals (17%), somewhat higher than previously reported rates of 8–10% with this tumor. At effective dosage levels, administration of the platinum complexes resulted in regressions at a significantly higher rate than would occur spontaneously. Administration at higher dosage levels yielded an increasingly larger number of deaths which are attributed to toxicity of the platinum complex.

Mice given single injections in the effective dose range began to lose weight after day 8 and until day 12 when they started to regain weight. The control tumor animals also began to lose weight about day 8 but usually continued to do so until death unless spontaneous regression of the tumors occurred. The size of the tumor remained static for a period of about 5 days after inoculation in animals treated with an effective dose, whereas the control tumors continued to increase in size. The tumors appear to have completely dropped out in about all of the surviving animals leaving an open wound in the tumored area. The skin then formed a flap and a scab slowly healing to a small scar which disappeared as hair grew over the area. The mice appeared healthy and no signs of irreversible damage were found on autopsy.

The previous experiment was repeated at the most effective dose level observed with a large group of animals consisting of 30 controls and 30 treated animals. Initial treatment began on day 8 after tumor implantation as before. The results of this test are shown below:

| Test Compound | Dose Schedule | Number of Mice | Deaths | Regressions |
|---|---|---|---|---|
| Cis-Pt(II)(NH$_3$)$_2$Cl$_2$ | 8.0 mg/kg on day 8 | 17 | 1 | 16 |
| | 8.0 mg/kg on day 8 and 4.0 mg/kg on day 24 | 9* | 6 | 3 |
| | | 26 | 7 | 19 |
| Controls (regressions spontaneous) | | 30 | 26 | 4 |

*Non-regressives after two weeks of initial treatment

The spontaneous regression rate in this experiment was 13%, slightly lower than the previous series. Deaths occurring in the control cages within the first 4 days after injection was attributed to tumor deaths and an equal number of deaths was subtracted from the treated group leaving 26 animals within the treatment category. Nine of the treated animals did not show any tumor regression within a two-week period after the initial injection and were given a second injection of the same compound at a dose of 4.0 mg/kg; 3 of these 9 then showed tumor regression. Thus, of the 26 treated animals, the test platinum compound effected significant regression in 19, significantly more than 13% spontaneous regression rate.

Other variations in our method will suggest themselves to those skilled in the art and our invention is as claimed.

We claim:

1. A method of treating animal malignant tumor cells sensitive to cis-Pt(II)(NH$_3$)$_2$Cl$_2$ in animals which comprises parenterally administering to an animal afflicted with said tumor cells a solution containing cis-Pt(II)(NH$_3$)$_2$Cl$_2$ in an amount sufficient to cause regression of the animal tumor cells.

2. A method according to claim 1 wherein the chloroplatinumammine is administered in multiple doses.

3. A method according to claim 1 wherein the chloroplatinumammine is administered in a single dose.

4. A method according to claim 1 wherein the chloroplatinumammine is administered in a saline salt-containing buffer solution.

* * * * *